(12) United States Patent
Henkelmann et al.

(10) Patent No.: US 6,534,669 B2
(45) Date of Patent: Mar. 18, 2003

(54) PREPARATION OF ALKENYLPHOSPHONIC ACID DERIVATIVES

(75) Inventors: Jochem Henkelmann, Mannheim (DE); Katrin Klass, Mannheim (DE); Jan-Dirk Arndt, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/985,114

(22) Filed: Nov. 1, 2001

(65) Prior Publication Data

US 2002/0077494 A1 Jun. 20, 2002

(30) Foreign Application Priority Data

Nov. 2, 2000 (DE) .......................... 100 54 218

(51) Int. Cl.⁷ .................................. C07F 9/06
(52) U.S. Cl. ...................... 558/137; 502/162
(58) Field of Search ................ 558/134, 137; 502/162

(56) References Cited

U.S. PATENT DOCUMENTS

| 3,673,285 A | 6/1972 | Lin |
| 3,681,481 A | 8/1972 | Lin ............ 260/970 |
| 3,972,923 A | 8/1976 | Finke et al. |
| 4,222,970 A | * 9/1980 | Montanari .......... 549/217 |
| 4,388,252 A | 6/1983 | Duersch et al. |
| 4,493,803 A | 1/1985 | Kleiner et al. |
| 5,210,177 A | * 5/1993 | Drent .............. 502/162 |
| 5,216,119 A | * 6/1993 | Klusener et al. ....... 502/162 |
| 5,693,826 A | 12/1997 | Tanaka et al. |
| 6,111,127 A | * 8/2000 | Tanaka et al. ......... 558/137 |

FOREIGN PATENT DOCUMENTS

| DE | 2132962 | 7/1971 |
| DE | 31 20 437 | 12/1982 |
| EP | 32 663 | 7/1981 |
| WO | 98/46613 | 10/1998 |
| WO | 99/67259 | 12/1999 |

OTHER PUBLICATIONS

CA:100:78868 abs of J Chem Soc Dalton Trans. by Bianchini et al (11) pp 2419–23 1983.*
CA:108:175728 abs of ACS Symp. Ser 363 (Catal. Act Carbon dioxide) by DuBois et al pp 42–51 1988.*

* cited by examiner

*Primary Examiner*—Jean F. Vollano
(74) *Attorney, Agent, or Firm*—Keil & Weinkauf

(57) ABSTRACT

Alkenylphosphonic acid derivatives are prepared by reacting phosphonic acid derivatives with alkynes in the presence of a metal complex catalyst system comprising (a) nickel and
(b) a phosphine having at least two trivalent phosphorus atoms.

9 Claims, No Drawings

PREPARATION OF ALKENYLPHOSPHONIC ACID DERIVATIVES

The present invention relates to a process for preparing alkenylphosphonic acid derivatives by reacting phosphonic acid derivatives with alkynes in the presence of a metal complex catalyst system.

Vinylphosphonic acid derivatives, in particular dialkyl vinylphosphonates are important as intermediates for the preparation of vinylphosphonic acids and as monomers for copolymerizations for producing adhesives and flame-resistant plastics.

Various methods are known for preparing them. The process described in DE-A 21 32 962 starts from ethylene oxide and phosphorus trichloride. The initial reaction product tris(2-chloroethyl) phosphite is rearranged at from 140 to 200° C. to form bis(2-chloroethyl) 2-chloroethanephosphonate and is then reacted with phosgene in the presence of a catalyst to form 2-chloroethanephosphonyl dichloride and vinylphosphonyl dichloride. Catalysts used are amines, heterocyclic nitrogen compounds, phosphines and also phosphine oxides.

EP 0 032 663 A2 describes a process for preparing vinylphosphonic acid derivatives in which dialkyl 2-acetoxyethanephosphonates are dissociated in the presence of acidic or basic catalysts. Basic catalysts proposed are tertiary amines and phosphines, ammonium salts or phosphonium salts, heterocyclic compounds and acid amides. A disadvantage of the process is the formation of a mixture of vinylphosphonic acid derivatives. The proportion of dialkyl vinylphosphonates is 23% at most.

An improved variant of this process described in DE 31 20 437 A1 comprises reacting the resulting product mixture with orthoesters of carboxylic acids to form dialkyl vinylphosphonates.

Disadvantages of the above processes are the formation of product mixtures, complicated multistage synthetic routes, the necessity of using high reaction temperatures and the use of chlorinated starting compounds. The large proportion of by-products, in particular, considerably impairs the process economics.

A further synthetic route for preparing diesters of alkenylphosphonic acids is the addition of alkynes onto diesters of phosphonic acid in the presence of a palladium complex catalyst. An advantage of this synthetic route is a pure addition reaction without formation of stoichiometric amounts of by-products or coproducts. U.S. Pat. No. 5,693,826 and WO 98/46613 disclose the addition in the presence of a palladium complex catalyst using phosphines and phosphites as ligands at temperatures less than or equal to 100°C. Wo 99/67259 and U.S. Pat. No. 6,111,127 specify bidentate phosphines as ligands. A disadvantage of these processes is the use of expensive noble metal catalysts.

U.S. Pat. No. 3,673,285 describes the addition of alkynes onto diesters of phosphonic acid to form diesters of alkenylphosphonic acids at from 130 to 200° C. in the presence of nickel complex catalysts selected from the group consisting of dicarbonylbis(triphenylphosphine)nickel(0), bis(tris(hydroxymethyl)phosphine)nickel(II) chloride, bis(tri-n-butylphosphine)nickel(II) bromide and tetracarbonylnickel(0). In the addition of ethyne onto diethyl phosphite, a yield of 40% of diethyl vinylphosphonate was achieved in the presence of bis(tri-n-butylphosphine)nickel (II) J bromide (Example 15). Disadvantages of this process are the low yield of significantly under 50% and the high reaction temperature of up to 200° C. required, which leads to exothermic decomposition of the ethyl phosphonate.

It is an object of the present invention to find a process for preparing alkenylphosphonic acid derivatives which does not have the abovementioned disadvantages, does not form any coproducts, allows a reaction temperature of significantly below 200° C., makes possible a high yield of significantly above 50% and makes do without use of an expensive noble metal catalyst.

We have found that this object is achieved by a process for preparing alkenylphosphonic acid derivatives by reacting phosphonic acid derivatives with alkynes in the presence of a metal complex catalyst system comprising a) nickel and b) a phosphine having at least two trivalent phosphorus atoms.

An essential feature of the process of the present invention is the presence of a metal complex catalyst system comprising (a) nickel and (b) a phosphine having at least two trivalent phosphorus atoms. Phosphines having two trivalent phosphorus atoms are generally referred to as diphosphines, phosphines having three trivalent phosphorus atoms are generally referred to as triphosphines, and so forth.

In general, the phosphines used in the process of the present invention have the formula (I)

where $R^1$, $R^2$, $R^3$ and $R^4$ are each, independently of one another, a carbon-containing organic radical and X is a carbon-containing organic bridging group.

For the purposes of the present invention, a carbon-containing organic radical is an unsubstituted or substituted, aliphatic, aromatic or araliphatic radical having from 1 to 30 carbon atoms. This radical may contain one or more hetero atoms such as oxygen, nitrogen, sulfur or phosphorus, for example —O—, —S—, —NR—, —CO—, —N=, —PR— and/or —PR$_2$, and/or be substituted by one or more functional groups containing, for example, oxygen, nitrogen, sulfur and/or halogen, for example by fluorine, chlorine, bromine, iodine and/or a cyano group (the radical R here is likewise a carbon-containing organic radical). If the carbon-containing organic radical contains one or more hetero atoms, it may also be bound via a hetero atom. Thus, for example, ether, thioether and tertiary amino groups are also included. The carbon-containing organic radical can be a monovalent or polyvalent, for example divalent, radical.

For the purposes of the present invention, a carbon-containing organic bridging group is an unsubstituted or substituted, aliphatic, aromatic or araliphatic divalent group having from 1 to 20 carbon atoms and from 1 to 10 atoms in the chain. The organic bridging group may contain one or more hetero atoms such as oxygen, nitrogen, sulfur or phosphorus, for example —O—, —S—, —NR—, —CO—, —N=, —PR— and/or —PR$_2$, and/or be substituted by one or more functional groups containing, for example, oxygen, nitrogen, sulfur and/or halogen, for example by fluorine, chlorine, bromine, iodine and/or a cyano group (the radical R here is likewise a carbon-containing organic radical). If the organic bridging group contains one or more hetero atoms, it may also be bound via a hetero atom. Thus, for example, ether, thioether and tertiary amino groups are also included.

In the process of the present invention, preference is given to using a phosphine (I) in which the radicals $R^1$, $R^2$, $R^3$ and $R^4$ are each, independently of one another,

- an unbranched or branched, acyclic or cyclic, unsubstituted or substituted alkyl radical having from 1 to 20 aliphatic carbon atoms, in which one or more of the $CH_2$ groups may also be replaced by hetero atoms such as —O— or by hetero atom-containing groups such as —CO— or —NR—, and in which one or more of the hydrogen atoms may be replaced by substituents such as aryl groups;
- an unsubstituted or substituted aromatic radical having one ring or two or three fused rings, in which one or more ring atoms may be replaced by hetero atoms such as nitrogen, and in which one or more of the hydrogen atoms may be replaced by substituents such as alkyl or aryl groups;

or in which the radicals $R^1$ together with $R^2$ and/or $R^3$ together with $R^4$ form

- an unsubstituted or substituted, aliphatic, aromatic or araliphatic group having from 3 to 10 atoms in the chain.

Examples of preferred monovalent radicals $R^1$, $R^2$, $R^3$ and $R^4$ are methyl, ethyl, 1-propyl, 2-propyl (sec-propyl), 1-butyl, 2-butyl (sec-butyl), 2-methyl-1-propyl (isobutyl), 2-methyl-2-propyl (tert-butyl), 1-pentyl, 2-pentyl, 3-pentyl, 2-methyl-2-butyl (tert-amyl), 1-hexyl, 2-hexyl, 3-hexyl, 2-methyl-2-pentyl, 3-methyl-3-pentyl, 2-methoxy-2-propyl, methoxy, ethoxy, 1-propoxy, 2-propoxy (sec-propoxy), 1-butoxy, 2-butoxy (sec-butoxy), 2-methyl-1-propoxy (isobutoxy), 2-methyl-2-propoxy (tert-butoxy), 1-pentoxy, 2-pentoxy, 3-pentoxy, 2-methyl-2-butoxy (tert-amoxy), 1-hexoxy, 2-hexoxy, 3-hexoxy, 2-methyl-2-pentoxy, 3-methyl-3-pentoxy, phenyl, 2-methylphenyl (o-tolyl), 3-methylphenyl (m-tolyl), 4-methylphenyl (p-tolyl), 2,6-dimethylphenyl, 2,4-dimethylphenyl, 2,4,6-trimethylphenyl, 2-methoxyphenyl, 3-methoxyphenyl, 4-methoxyphenyl, 2-pyridyl, 3-pyridyl, 4-pyridyl, 3-pyridazinyl, 4-pyridazinyl, 5-pyridazinyl, 2-pyrimidinyl, 4-pyrimidinyl, 5-pyrimidinyl, 2-pyrazinyl, 2-(1,3,5-triazin) yl, 1-naphthyl, 2-naphthyl, 2-quinolyl, 8-quinolyl, 1-isoquinolyl and 8-isoquinolyl. Examples of preferred divalent radicals $R^1$ together with $R^2$ and/or $R^3$ together with $R^4$ are 1,4-butylene, 1,4-dimethyl-1,4-butylene, 1,1,4,4-tetramethyl-1,4-butylene, 1,4-dimethoxy-1,4-butylene, 1,4-dimethyl-1,4-dimethoxy-1,4-butylene, 1,5-pentylene, 1,5-dimethyl-1,5-pentylene, 1,5-dimethoxy-1,5-pentylene, 1,1,5,5-tetramethyl-1,5-pentylene, 1,5-dimethyl-1,5-dimethoxy-1,5-pentylene, 3-oxa-1,5-pentylene, 3-oxa-1,5-dimethyl-1,5-pentylene, 3-oxa-1,5-dimethoxy-1,5-pentylene, 3-oxa-1,1,5,5-tetramethyl-1,5-pentylene, 3-oxa-1,5-dimethyl-1,5-dimethoxy-1,5-pentylene,

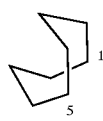
1,5-cyclooctylene

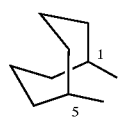
1,5-dimethyl-1,5-cyclooctylene

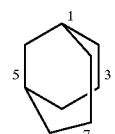
3,7-bicyclo-[3.3.1]nonylene

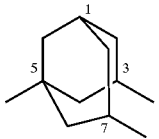
1,3,5,7-tetramethyl-3,7-bicyclo[3.3.1]nonylene,

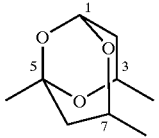
4,8,9-trioxa-1,3,5,7-tetramethyl-3,7-bicyclo[3.3.1] nonylene.

The process of the present invention is particularly preferably carried out using a phosphine (I) in which $R^1$, $R^2$, $R^3$ and/or $R^4$ are each, independently of one another, an unsubstituted or substituted $C_3$–$C_{12}$-alkyl radical in which at most one atom from the group consisting of hydrogen, fluorine, chlorine, bromine and iodine is bound to the α-carbon atom; and/or in which $R^1$, $R^2$, $R^3$ and/or $R^4$ are each, independently of one another, an unsubstituted or substituted aromatic radical having 6 ring atoms in which one, two or three ring atoms may be replaced by nitrogen; and/or in which $R^1$ together with $R^2$ and/or $R^3$ together with $R^4$ form an unsubstituted or substituted, aliphatic, aromatic or araliphatic group having from 4 to 7 atoms in the chain and a total of not more than 30 carbon atoms.

The unsubstituted or substituted $C_3$–$C_{12}$-alkyl radical in which not more than one atom from the group consisting of hydrogen, fluorine, chlorine, bromine and iodine is bound to the α-carbon atom is an α-branched alkyl radical. At least two further carbon atoms are preferably bound to the α-carbon atom. The third atom bound to the α-carbonatom is preferably hydrogen, carbon or a hetero atom, for example oxygen, nitrogen or sulfur. Preferred examples are 2-propyl (sec-propyl), 2-butyl (sec-butyl), 2-methyl-2-propyl (tert-butyl), 2-methyl-2-butyl (tert-amyl) and 2-methoxy-2-propyl.

Preferred examples of an unsubstituted or substituted aromatic radical having 6 ring atoms in which one, two or three ring atoms may be replaced by nitrogen are phenyl, 2-methylphenyl (o-tolyl), 3-methylphenyl (m-tolyl), 4-methylphenyl (p-tolyl), 2,6-dimethylphenyl, 2,4-dimethylphenyl, 2,4,6-trimethylphenyl and 2-pyridyl.

Preferred examples of divalent radicals $R^1$ together with $R^2$ and/or $R^3$ together with $R^4$ are 1,1,4,4-tetramethyl-1,4-butylene, 1,4-dimethyl-1,4-dimethoxy-1,4-butylene, 1,1,5,5-tetramethyl-1,5-pentylene, 1,5-dimethyl-1,5-dimethoxy-1,5-pentylene, 1,5-dimethyl-1,5-cyclooctylene, 1,3,5,7-tetramethyl-3,7-bicyclo[3.3.1]nonylene and 4,8,9-trioxa-1,3,5,7-tetramethyl-3,7-bicyclo[3.3.1]nonylene.

Very particular preference is given to using a phosphine (I) in which the radicals $R^1$, $R^2$, $R^3$ and $R^4$ are each a 2-methyl-2-propyl (tert-butyl) group or a phenyl group in the process of the present invention.

The process of the present invention is preferably carried out using a phosphine (I) in which X is an unsubstituted or substituted, aliphatic, aromatic or araliphatic group having from 1 to 8 atoms, preferably from 2 to 4 atoms, in the chain and a total of not more than 20 carbon atoms. In this group, one or more of the $CH_2$ groups may be replaced by hetero atoms such as —O— or by hetero atom—containing groups such as —CO— or —NR—, and/or one or more of the aromatic ring atoms may be replaced by hetero atoms such as nitrogen.

Examples of preferred bridging groups X are 1,2-ethylene, 1,3-propylene, 1,2-propylene, 1,4-butylene, 2-methyl-1,3-propylene, 1,5-pentylene, 2,2-dimethyl-1,3-propylene, 1,6-hexylene, —O—CH$_2$CH$_2$—O—, —O—CH$_2$CH$_2$CH$_2$—O—, o-phenylene, o-xylene or 2,2'-biphenylene.

In the process of the present invention, particular preference is given to using a phosphine (I) in which the bridging group X is a 1,2-ethylene, 1,3-propylene, 1,4-butylene or o-xylene group.

The process of the present invention is very particularly preferably carried out using a phosphine (I) in which the radicals $R^1$ to $R^4$ are each a 2-methyl-2-propyl (tert-butyl) group or a phenyl group and X is a 1,2-ethylene, 1,3-propylene, 1,4-butylene or o-xylene group. Very particularly preferred examples are 1,2-bis(di-tert-butylphosphino)ethane, 1,2-bis(diphenylphosphino)ethane, 1,3-bis(di-tert-butyl-phosphino)propane, 1,3-bis(diphenylphosphino)propane, 1,4-bis(di-tert-butylphosphino)butane, 1,4-bis(diphenyl-phosphino)butane, bis(di-tert-butylphosphino)-o-xylene and bis(diphenylphosphino)-o-xylene, in particular 1,3-bis(di-tert-butylphosphino)propane and 1,3-bis(diphenylphosphino)propane.

The synthesis of diphosphines is generally known and is described, for example, in L. Brandsma et al., "Application of Transition Metal Catalysts in Organic Synthesis", Springer-Verlag, Berlin 1997, pages 6 to 9.

In the process of the present invention, the metal complex catalyst system is generally prepared by combining an Ni complex and the phosphine or by combining an Ni(II) compound, a reducing agent and the phosphine. Since the phosphine can also act as reducing agent, the metal complex catalyst system is also obtainable by combining an Ni(II) compound and the phosphine without a further reducing agent.

Ni complexes suitable for carrying out the first-named variant H are in principle all Ni complexes which react with the phosphine under the reaction conditions to form the metal complex catalyst system. Examples of suitable Ni complexes are tetracarbonylnickel, bis(cycloocta-1,5-diene)nickel, (cyclododeca-1,5,9-triene)nickel, dimethylbipyridylnickel and dimethylbis(triphenylphosphine)nickel.

The Ni(II) compounds required for the second-named variant can be inorganic or organic in nature or be of mixed nature. Examples which may be mentioned are nickel(II) halides, nickel(II) sulfate, nickel(II) acetylacetonate, 1,3-bis(diphenylphosphino)propanenickel(II) chloride, hexamminenickel(II) chloride and nickel(II) bromide diethylene glycol dimethyl ether complexes. Suitable reducing agents are, for example, elemental zinc, trialkylboron compounds, trialkylaluminum compounds, diisobutylaluminum hydride and phosphines.

The metal complex catalyst system can be prepared in a separate step before the actual alkenylation of the phosphonic acid derivative or else in-situ by combining the components mentioned. As solvent, use is generally made of the phosphonic acid derivative as long as this is liquid under the reaction conditions. However, it is also possible and may be advantageous to prepare the metal complex catalyst system in the presence of a further, inert solvent. In this case, preference is then given to using the same solvents which can also be used as solvents for the alkenylation reaction and are described further below.

In the process of the present invention, use is generally made of a molar ratio of the phosphine to the nickel of the metal complex catalyst system of from 0.5 to 6, preferably from 1 to 4 and particularly preferably from 1.5 to 2.5.

The molar ratio of the nickel of the metal complex catalyst system to the phosphorus of the phosphonic acid derivative and the products formed therefrom is generally from 0.01 to 10%, preferably from 0.05 to 5% and particularly preferably from 0.5 to 3%, in the process of the present invention.

The process of the present invention can be carried out at from 0 to 200° C., preferably from 20 to 150° C. and particularly preferably from 50 to 120° C. It is generally carried out at a pressure of from 0.01 to 5 MPa abs, preferably from 0.05 to 2.5 MPa abs, in particular at atmospheric pressure.

The process of the present invention can be carried out in the absence of an additional solvent ("solvent-free") or in the presence of an inert solvent. For the purposes of the present invention, inert solvents are solvents which do not react chemically with the compounds used under the reaction conditions set. Suitable inert solvents are, for example, tetrahydrofuran, 1,4-dioxane, N-methylpyrrolidone, N-methylpiperidone, dimethyl sulfoxide, toluene, xylene, glycol ethers (e.g. 1,2-dimethoxyethane (ethylene glycol dimethyl ether), bis(2-methoxyethyl) ether (diethylene glycol dimethyl ether), triethylene glycol dimethyl ether or tetraethylene glycol dimethyl ether), dimethylformamide, dimethylformanilide and mixtures thereof. The addition of an inert solvent may be advantageous, for example when using relatively high molecular weight or viscous phosphonic acid derivatives or phosphonic acid derivatives which are solid under the reaction conditions.

It is likewise advantageous to carry out the process of the present invention in the presence of a free-radical inhibitor as an additive. Free-radical inhibitors which are suitable in principle are the inhibitors generally customary in industry, for example N,N'-bis(1-methylpropyl)-1,4-phenylenediamine, 2,6-di-tert-butyl-4-methylphenol or 1,2-dihydroxybenzene (catechol). If a free-radical inhibitor is used, it is generally used in such an amount that the molar ratio of the free-radical inhibitor and the phosphorus of the phosphonic acid derivative and the products formed therefrom is from 0.01 to 10%, preferably from 0.05 to 5% and particularly preferably from 0.5 to 3%.

The phosphonic acid derivatives to be used in the process of the present invention are generally known and have, for example, the formula (II)

(II)

Phosphonic acid derivatives of the formula (II) are generally prepared by reacting phosphorus trichloride with the appropriate alcohols and/or the appropriate phenols. Further details may be found, for example, in Ullmann's Encyclopedia of Industrial Chemistry, 6$^{th}$ edition, 1999 Electronic Release, Chapter "Phosphorus Compounds, Organic Phosphites and Hydrogenphosphonates".

In the process of the present invention, preference is given to using a phosphonic acid derivative (II) in which the radicals $R^5$ and $R^6$ are each, independently of one another, an unbranched or branched, acyclic or cyclic, unsubstituted or substituted alkyl radical having from 1 to 20 aliphatic carbon atoms, in which one or more of the CH₂ groups may also be replaced by hetero atoms such as —C— or by hetero atom-containing groups such as —CO— or —NR—, and in which one or more of the hydrogen atoms may be replaced by substituents such as aryl groups;

an unsubstituted or substituted aromatic radical having one ring or two or three fused rings, in which one or more ring atoms may be replaced by hetero atoms such as nitrogen, and in which one or more of the hydrogen atoms may be replaced by substituents such as alkyl or aryl groups;

or in which the radical $R^5$ together with $R^6$ forms an unbranched or branched, acyclic or cyclic, unsubstituted or substituted $C_4$–$C_{20}$-alkylene radical having from 4 to 10 atoms in the alkylene chain, in which CH₂ groups may also be replaced by hetero groups such as —CO—, —O— or —NR— and in which one or more of the hydrogen atoms may be replaced by substituents such as aryl groups.

Examples of preferred radicals $R^5$ and $R^6$ are $C_1$–$C_{12}$-alkyl, particularly preferably methyl, ethyl, 1-propyl, 2-propyl, 1-butyl, 2-butyl, 2-methyl-1-propyl, 2-methyl-2-propyl, 1-pentyl, 1-hexyl, 1-octyl, 2-ethyl-1-hexyl, 1-decyl and 1-dodecyl;

$C_6$–$C_{10}$-aryl, particularly preferably phenyl;

$C_7$–$C_{10}$-aralkyl, particularly preferably phenylmethyl; and $C_7$–$C_{10}$-alkaryl, particularly preferably 2-methylphenyl, 3-methylphenyl and 4-methylphenyl.

The phosphonic acid derivative used in the process of the present invention is very particularly preferably the dimethyl ester, the diethyl ester, the dipropyl ester, the dibutyl ester, the di(2-ethylhexyl) ester or the diphenyl ester of phosphonic acid.

The alkynes to be used in the process of the present invention have the formula (III)

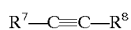  (III), where $R^7$ and $R^8$ are each, independently of one another, hydrogen or a carbon-containing organic radical. $R^7$ and $R^8$ may also be joined to one another. The term "carbon-containing organic radical" is defined as above in the definition of the radicals $R^1$ to $R^4$ in the formula (I), with the radical being monovalent or divalent in the present case.

In the process of the present invention, preference is given to using an alkyne (III) in which the radicals $R^7$ and $R^8$ are each, independently of one another, hydrogen;

an unbranched or branched, acyclic or cyclic, unsubstituted or substituted alkyl radical having from 1 to 20 aliphatic carbon atoms, in which one or more of the CH₂ groups may also be replaced by hetero atoms such as —O— or by hetero atom-containing groups such as —CO— or —NR—, and in which one or more of the hydrogen atoms may be replaced by substituents such as aryl groups;

an unsubstituted or substituted aromatic radical having one ring or two or three fused rings, in which one or more ring atoms may be replaced by hetero atoms such as nitrogen, and in which one or more of the hydrogen atoms may be replaced by substituents such as alkyl or aryl groups.

Examples of preferred radicals $R^7$ and $R^8$ are hydrogen;

$C_1$–$C_{10}$-alkyl, particularly preferably methyl, ethyl, 1-propyl, 1-butyl, 1-pentyl and 1-hexyl;

$C_6$–$C_{10}$-aryl, particularly preferably phenyl;

$C_7$–$C_{10}$-aralkyl, particularly preferably phenylmethyl; and $C_7$–$C_{10}$-alkaryl, particularly preferably 2-methylphenyl, 3-methylphenyl and 4-methylphenyl.

Very particular preference is given to using ethyne or propyne as alkynes in the process of the present invention.

The process of the present invention is very particularly preferably employed for preparing dimethyl ethenylphosphonate, diethyl ethenylphosphonate, di-n-propyl ethenylphosphonate and di-n-butyl ethenylphosphonate.

The process of the present invention can be carried out batchwise, semicontinuously or continuously.

In a general embodiment for carrying it out batchwise, the phosphine, the Ni complex (or the Ni(II) compound and the reducing agent), the phosphonic acid derivative, the alkyne, any solvent used and any free-radical inhibitor used are combined, mixed and brought to the reaction conditions. After the reaction is complete, the mixture is passed on to work-up, preferably by distillation, and the desired alkenylphosphonic acid derivative is isolated.

In a general embodiment for carrying out the process semicontinuously, the phosphine, the Ni complex (or the Ni(II) compound and the reducing agent), the phosphonic acid derivative, any solvent used and any free-radical inhibitor used are combined, mixed and brought to the reaction temperature. The alkyne is then introduced continuously until the desired amount has been reached. It can be introduced in gaseous or liquid form. If it is added in liquid form, pure, liquid alkyne or a solution in a solvent can be used. After the introduction of alkyne is complete, the reaction mixture can be maintained under the reaction conditions for a further period. After the reaction is complete, the reaction mixture is passed on to work-up, preferably by distillation, and the desired alkenylphosphonic acid derivative is isolated.

In a general embodiment for carrying out the process continuously, the phosphine, the Ni complex (or the Ni(II) compound and the reducing agent), any solvent used and any free-radical inhibitor used are combined, mixed and brought to the reaction temperature. The phosphonic acid derivative and the alkyne are then metered in continuously in the desired ratio. In general, the phosphonic acid derivative is added in liquid form, if desired as a solution in a solvent. The alkyne can be added in gaseous or liquid form. When it is added in liquid form, pure, liquid alkyne or else a solution in a solvent can be used. Liquid reaction mixture is continuously taken off and the alkenylphosphonic acid derivative formed is isolated in a downstream step, for example by distillation or extraction. Relatively high-boiling by-products may also be separated off. The remaining mixture comprising mainly unreacted phosphonic acid derivative and any solvent used may be recirculated.

The process of the present invention makes it possible to prepare alkenylphosphonic acid derivatives at a reaction temperature below 150° C. without use of an expensive noble metal catalyst in only one synthesis step starting from readily available starting compounds. Since the reaction is a very selective addition reaction, no coproducts and only a small amount of by-products are formed. The process of the present invention makes it possible to achieve a high yield of significantly above 50% with good process economics.

EXAMPLES

Experimental Procedure 1 (Ni(0) Complex/atmospheric Pressure)

In Experimental Procedure 1, 0.1 mol of the phosphonic diester, 2 mol % of bis(cycloocta-1,5-diene)nickel and 4 mol % of the diphosphine ligand (or 8 mol % of the monophosphine ligand) were placed under oxygen- and water-free conditions in a round-bottom flask equipped with a reflux condenser. In some cases, 2 mol % of 2,6-di-tert-butyl-4-methylphenol as additive and/or 80 ml of an inert solvent were added. For the reaction with liquid alkynes, these were added in liquid form and the liquid mixture was heated to 100° C. while stirring. For the reaction with gaseous alkynes, these were passed directly (6 standard l/h) into the liquid and the liquid mixture was heated to 100° C. while stirring.

Experimental Procedure 2 (Ni(0) Complex/superatmospheric pressure)

In Experimental Procedure 2, 0.1 mol of the phosphonic diester, 2 mol % of bis(cycloocta-1,5-diene)nickel, 4 mol % of the diphosphine ligand and 2 mol % of 2,6-di-tert-butyl-4-methylphenol as additive were placed under oxygen- and water-free conditions in an autoclave. The mixture was subsequently heated to 100° C. and the autoclave was pressurized with ethyne to 2.0 MPa abs. The amount of ethyne taken up during the reaction was replaced to keep the pressure constant.

Experimental Procedure 3 (nickel(II) compound/atmospheric pressure)

In Experimental Procedure 3, 0.1 mol of the phosphonic diester and, depending on the metal complex catalyst system used (3a to 3c, see below), appropriate amounts of Ni(II) compound and diphosphine or monophosphine were placed under oxygen- and water-free conditions in a round-bottom flask equipped with a reflux condenser. In some cases, 2 mol % of 2,6-di-tert-butyl-4-methylphenol as additive and/or 80 ml of an inert solvent were added. For the reaction with gaseous alkynes, these were passed directly (6 standard l/h) into the liquid and the liquid mixture was heated to 100° C. while stirring.

The following metal complex catalyst systems were used:

Experimental Procedure 3a: 2 mol % of bis(triphenylphosphine)-nickle(II) chloride 4 mol % of triphenylphosphine Experimental Procedure 3b: 2 mol % of 1,3-bis(diphenylphosphino)-propanenickel(II) chloride 2 mol % of 1,3-bis(diphenylphosphino)-propane Experimental Procedure 3c: 2 mol % of hexamminenickel(II) chloride 4 mol % of 1,3-bis(diphenylphosphino)-propane Experimental Procedure 4 [Ni(acad)$_2$, dppp, atmospheric pressure]

In Experimental Procedure 4, 0.65 mol of the phosphonic diester together with 63 ml of tetraethylene glycol dimethyl ether and 2 mol % of nickel(II) acetylacetonate (Ni(acac)$_2$) and 4 mol % of the diphosphine ligand 1,3-bis(diphenylphosphino)propane (dppp) were placed under oxygen- and water-free conditions in a flask equipped with a reflux condenser. In one case, 2 mol % of 2,6-di-tert-butyl-4-methylphenol were added as additive to the reaction mixture. For the reaction with ethyne, the gas was passed directly into the liquid (12 standard l/h) and the liquid mixture was heated to 100° C. while stirring.

The analyses in both variants of the experimental procedure were carried out by gas chromatography. Unless indicated otherwise, absolute determinations were carried out and the conversion of the phosphonic diester, the selectivity to the alkenylphosphonic diester and the yield of the alkenylphosphonic diester were calculated therefrom.

Examples 1 to 19

An overview of Examples 1 to 19 is given in Tables 1 and 2.

When using phenylacetylene (R'=phenyl, Example 9) and 1-octyne (R'=hexyl, Example 10), three isomeric alkenylphosphonic diesters were formed as reaction products according to the following reaction equation.

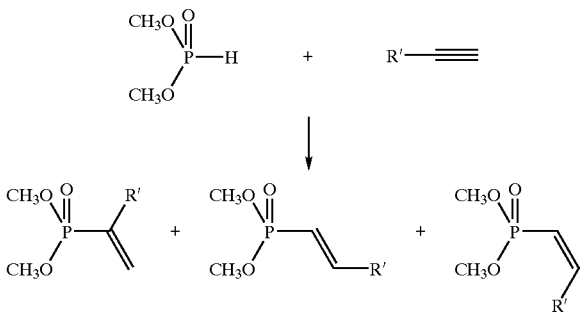

In Comparative Example 1 using triphenylphosphine (tpp) as ligand of the metal complex catalyst system, a yield of dimethyl ethenylphosphonate of only 5% was achieved after a reaction time of one hour. In Examples 3 and 5 according to the present invention using 1,4-bis(diphenylphosphino)butane (dppb) and 1,3-bis(diphenylphosphino)propane (dppp) as ligand, significantly higher yields of 65% and 80% were achieved under otherwise identical conditions.

Comparison of the examples according to the present invention 2 with 3, 4 with 5 and 6 with 7 shows the positive influence of a free-radical inhibitor as additive. An about 10% relative higher yield was achieved in the presence of 2,6-di-tert-butyl-4-methylphenol as additive under otherwise identical conditions.

Examples 4 to 8 according to the present invention show that the reaction can be carried out in high yield both in the presence of a solvent and in the absence of a solvent.

Examples 7 and 11 according to the present invention show that the reaction leads to a high yield both under atmospheric pressure and under superatmospheric pressure.

In Comparative Example 14 using triphenylphosphine (tpp) as ligand of the metal complex catalyst system, a yield of dimethyl ethenylphosphonate of only 0.2% was achieved after a reaction time of 6 hours. In Example 15 according to the present invention using 1,3-bis(diphenylphosphino)propane (dppp) as ligand, a significantly higher yield of 49% was achieved after a reaction time of only one hour.

Examples 15 to 17 according to the present invention show that the reaction can be carried out in a high yield both in the presence of a solvent and in the absence of a solvent.

Examples 18 and 19 according to the present invention show that the use of nickel(II) acetylacetonate as nickel(II) source leads to a virtually complete conversion of 98–99% together with a high selectivity of 87–89% after a reaction time of only 1.5 hours. A high yield of 86–87% was able to be achieved. Furthermore, Example 19 shows that a high yield of 87% can be achieved even in the absence of an additive. The use of the solvent tetraethylene glycol dimethyl ether results, owing to the greater difference between the boiling points of desired product and solvent, in a simpler separation which gives a better product purity.

TABLE 1

Overview of Examples 1 to 10

| Ex. | Experimental procedure | Phosphonic acid compound | Alkyne | Phosphine ligand | Additive | Solvent | Reaction time [h] | Conversion [%] | Selectivity [%] | Yield [%] |
|---|---|---|---|---|---|---|---|---|---|---|
| 1* | 1 | DMP | Ethyne | tpp | yes | TEGDME | 1 | 30 | 16 | 5 |
| 2 | 1 | DMP | Ethyne | dppb | no | TEGDME | 5 | 90 | 64 | 58 |
| 3 | 1 | DMP | Ethyne | dppb | yes | TEGDME | 1 | 89 | 73 | 65 |
| 4 | 1 | DMP | Ethyne | dppp | no | TEGDME | 1 | 95 | 78 | 74 |
| 5 | 1 | DMP | Ethyne | dppp | yes | TEGDME | 1 | 95 | 84 | 80 |
| 6 | 1 | DMP | Ethyne | dppp | no | none | 1 | 98 | 79 | 77 |
| 7 | 1 | DMP | Ethyne | dppp | yes | none | 1 | 99 | 86 | 85 |
| 8 | 1 | DMP | Ethyne | dppp | yes | THF | 3 | 98 | 85 | 83 |
| 9 | 1 | DMP | Phenyl-acetylene | dppp | yes | TEGDME | 1 | 98[1)2)] | 96[1)2)] | 94[1)2)] |
| 10 | 1 | DMP | 1-Octyne | dppp | yes | TEGDME | 1 | 98[1)2)] | 90[1)2)] | 88[1)2)] |

*Comparative example
[1)]Calculated from GC % by area
[2)]of the sum of all three alkenylphosphonic diester isomers
DMP: Dimethyl phosphonate
DEP: Diethyl phosphonate
tpp: Triphenylphosphine
dppb: 1,4-bis(diphenylphosphino)butane
dppp: 1,3-bis(diphenylphosphino)propane
TEGDME: Triethylene glycol dimethyl ether
THF: Tetrahydrofuran

TABLE 2

TETGDME: Tetraethylene glycol dimethyl ether
Overview of Examples 11 to 19

| Ex. | Experimental procedure | Phosphonic acid compound | Alkyne | Phosphine ligand | Additive | Solvent | Reaction time [h] | Conversion [%] | Selectivity [%] | Yield [%] |
|---|---|---|---|---|---|---|---|---|---|---|
| 11 | 2 | DMP | Ethyne | dppp | yes | none | 1 | 89[1)] | 83[1)] | 74[1)] |
| 12 | 1 | DEP | Ethyne | dppp | yes | TEGDME | 6 | 94[1)] | 68[1)] | 64[1)] |
| 13 | 1 | DEP | Ethyne | dppp | yes | none | 2 | 98[1)] | 81[1)] | 79[1)] |
| 14* | 3a | DMP | Ethyne | tpp | yes | TEGDME | 6 | 24 | 1 | 0.2 |
| 15 | 3b | DMP | Ethyne | dppp | yes | TEGDME | 1 | 75 | 65 | 49 |
| 16 | 3b | DMP | Ethyne | dppp | yes | none | 2 | 97 | 72 | 70 |
| 17 | 3c | DMP | Ethyne | dppp | yes | TEGDME | 4 | 84 | 68 | 57 |
| 18 | 4 | DMP | Ethyne | dppp | yes | TETGDME | 1.5 | 99 | 87 | 86 |
| 19 | 4 | DMP | Ethyne | dppp | no | TETGDME | 1.5 | 98 | 89 | 87 |

*Comparative example
[1)]Calculated from GC % by area
[2)]of the sum of all three alkenylphosphonic diester isomers
DMP: Dimethyl phosphonate
DEP: Diethyl phosphonate
tpp: Triphenylphosphine
dppb: 1,4-bis(diphenylphosphino)butane
dppp: 1,3-bis(diphenylphosphino)propane
TEGDME: Triethylene glycol diethyl ether
THF: Tetrahydrofuran
TETGDME: Tetraethylene glycol dimethyl ether

We claim:

1. A process for preparing alkenylphosphonic acid derivatives by reacting phosphonic acid derivatives of the formula (II)

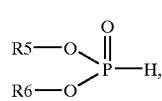

(II)

where

R$^5$ and R$^6$ are each, independently of one another,
an unbranched or branched, acyclic or cyclic, unsubstituted or substituted alkyl radical having from 1 to 20 aliphatic carbon atoms, in which one or more of the CH$_2$ groups may also be replaced by hetero atoms such as —O— or by hetero atom-containing groups such as —CO— or —NR—, and in which one or more of the hydrogen atoms may replaced by substituents such as aryl groups;
an unsubstituted or substituted aromatic radical having one ring, or two or three fused rings, in which one or more ring atoms may be replaced by hetero atoms such as nitrogen, and in which one or more of the hydrogen atoms may be replaced by substituents such as alkyl or aryl groups;
or in which the radical R$^5$ together with R$^6$ forms
an unbranched or branched, acyclic or cyclic, unsubstituted or substituted C$_4$–C$_{20}$-alkylene radical having from 4 to 10 atoms in the alkylene chain, in which CH$_2$ groups may also be replaced by hetero groups such as —CO—, —O— or —NR— and in which one or more of the hydrogen atoms may be replaced by substituents such as aryl groups;
with alkynes of the formula (III)

where R$^7$ and R$^8$ are each, independently of one another, hydrogen or a carbon-containing organic radical, in the presence of a metal complex catalyst system comprising
(a) nickel and
(b) a phosphine of the formula (I)

where R$^1$, R$^2$, R$^3$ and R$^4$ are each, independently of one another, a carbon-containing organic radical and X is a carbon-containing organic bridging group.

2. A process as claimed in claim 1, wherein the metal complex catalyst system comprises a phosphine of the formula (I) in which R$^1$, R$^2$, R$^3$ and/or R$^4$ are each, independently of one another, an unsubstituted or substituted C$_3$–C$_{12}$-alkyl radical in which not more than one atom from the group consisting of hydrogen, fluorine, chlorine, bromine and iodine is bound to the α-carbon atom; and/or in which R$^1$, R$^2$, R$^3$ and/or R$^4$ are each, independently of one another, an unsubstituted or substituted aromatic radical having 6 ring atoms in which one, two or three ring atoms may be replaced by nitrogen; and/or in which R$^1$ together with R$^2$ and/or R$^3$ together with R$^4$ form an unsubstituted or substituted, aliphatic, aromatic or araliphatic group having from 4 to 7 atoms in the chain and a total of not more than 30 carbon atoms.

3. A process as claimed in claim 1, wherein the metal complex catalyst system used comprises a phosphine of the formula (I) in which X is an unsubstituted or substituted, aliphatic, aromatic or araliphatic group having from 1 to 8 atoms in the chain and a total of not more than 20 carbon atoms.

4. A process as claimed in claim 1, wherein the metal complex catalyst system used comprises a phosphine of the formula (I) in which R$^1$ to R$^4$ are each a 2-methyl-2-propyl group or each a phenyl group and X is a 1,2-ethylene, 1,3-propylene, 1,4-butylene or o-xylene group.

5. A process as claimed in claim 1, wherein the metal complex catalyst system is prepared by combining an Ni complex and the phosphine or by combining an Ni(II) compound, a reducing agent and the phosphine.

6. A process as claimed in claim 1, wherein the molar ratio of the nickel of the metal complex catalyst system to the phosphorus of the phosphonic acid derivative and the products formed therefrom is from 0.01 to 10%.

7. A process as claimed in claim 1, wherein the reaction is carried out at from 20 to 150° C. and a pressure of from 0.05 to 2.5 MPa abs.

8. A process as claimed in claim 1, wherein the phosphonic acid derivative used is the dimethyl ester, the diethyl ester, the dipropyl ester, the dibutyl ester, the di(2-ethylhexyl) ester or the diphenyl ester of phosphonic acid.

9. A process as claimed in claim 1, wherein the alkyne used is ethyne or propyne.

* * * * *